United States Patent [19]

Zemo

[11] Patent Number: 5,295,480

[45] Date of Patent: Mar. 22, 1994

[54] TRACHEAL TUBE SUPPORT MECHANISM

[76] Inventor: Harry Zemo, 6910 Forman Way, Sacramento, Calif. 95828

[21] Appl. No.: 894,293

[22] Filed: Jun. 4, 1992

[51] Int. Cl.⁵ ............................................. A61M 16/00
[52] U.S. Cl. .................... 128/207.17; 128/DIG. 26; 24/543
[58] Field of Search .................. 128/200.24, 207.14, 128/207.17, DIG. 26; 24/543

[56] References Cited

U.S. PATENT DOCUMENTS

| | | | |
|---|---|---|---|
| 3,987,798 | 10/1876 | McGinnis | 128/207.17 |
| 4,193,174 | 3/1980 | Stephens | 24/543 X |
| 4,220,301 | 9/1980 | Jacobs et al. | 24/543 X |
| 4,470,179 | 9/1984 | Gollin | 24/543 |
| 4,537,192 | 8/1985 | Foster | 128/207.17 |
| 4,744,358 | 5/1988 | McGinnis | 128/207.17 |
| 5,230,489 | 7/1993 | White | 24/543 X |

OTHER PUBLICATIONS

Hudson Oxygen Therapy Co. Brochure, Model #1065 Tracheal Tube Holder, Oct. 1980.
"A New Endo Tracheal Catheter Fixation", Frey, R., Brit. J. Anaesth., (1955) vol. 27, p. 260.

Primary Examiner—Edgar S. Burr
Assistant Examiner—Eric P. Raciti
Attorney, Agent, or Firm—Mark C. Jacobs

[57] ABSTRACT

A mechanism for supporting a tracheal tube within the mouth of a user. The mechanism utilizes a facial cover. The facial cover is provided with a first portion which extends over the nasal bridge of the user and a second portion which extends over the chin of the user. The first and second portions are connected to one another leaving an opening for access to the nose and mouth of the user. The tracheal tube is suspended within the mouth of the user by an element, such as a bar, which extends and is linked to the facial cover. The bar possesses a requisite degree of rigidity to provide such support.

4 Claims, 2 Drawing Sheets

TRACHEAL TUBE SUPPORT MECHANISM

BACKGROUND OF THE INVENTION

The present invention relates to a tracheal tube support mechanism for holding a tracheal tube within the mouth of the user.

Tracheal tubes are often required during medical treatment where the patient is rendered or becomes unconscious. It is important that a tracheal tube be placed through the mouth of the patient and into the trachea to maintain a clear passage for air to the lungs of the patient. The tracheal tube generally prevents body secretions, vomitus, or a laryngo spasm from closing this vital air passageway.

Unfortunately, anesthetized patients coming into a conscious state often attempt to remove the tracheal tubes since they irritate and are somewhat painful to the patient. In addition, patients attempting to scratch their nose or rub their eyes, incidently remove tracheal tubes from their position. In the past, patients have been fettered to prevent them from touching the tracheal tube. Adhesive tape has been employed to hold the tracheal tube to the face of the user. This method is unreliable and tends to bloody the lips of the patient during use.

A method for holding a tracheal tube in place would be a notable advance in the medical field.

SUMMARY OF THE INVENTION

In accordance with the present invention, a novel and useful mechanism for supporting a tracheal tube is herein provided.

The mechanism of the present invention utilizes a facial cover which may be constructed of relatively pliable material. The facial cover includes a first portion which extends over the nasal bridge of the user and a connected second portion which passes over the chin of the user. A strap mechanism or similar holding apparatus fastens the facial cover around the head of the user. Such means for holding the facial cover to the head of the user may take the form of an adjustable strap. The facial cover is formed to include an opening surrounding the nose and lips of the user to allow access to the same by the patient and doctor.

The support mechanism of the present invention further possesses means for positioning the tracheal tube within the mouth of the user which resists removal of the same from the mouth. Such positioning means includes an element which is linked to the facial cover and is held to the tracheal tube. The element connects to the facial cover at one portion or at two portions on either side of the nose of the user. A fastener may be employed to link the element to the tracheal tube. The fastener would resist any sliding movement of the tracheal tube relative to the element and, thus, hold the tracheal tube in place.

It may be apparent that a novel and useful tracheal tube support mechanism has been herein described.

It is therefore an object of the present invention to provide a tracheal tube support mechanism which firmly holds a tracheal tube in position relative to the mouth of the user to prevent intentional or accidental removal of the tracheal tube by the patient.

It is another object of the present invention to provide a tracheal tube support mechanism which includes a facial cover that permits access to the nose and lips of the user when in place.

A further object of the present invention is to provide a tracheal tube support mechanism which is fully adjustable and easily assembled for use on a patient.

A further object of the present invention is to provide a tracheal tube support mechanism in which is comfortable to the patient and does not irritate or pain the patient when it is used.

Yet another object of the present invention is to provide a tracheal tube support mechanism which eliminates the need to immobilize the patients arms when the tracheal tube is in use.

The invention possesses other objects and advantages, especially as concerns particular characteristics and features thereof which will become apparent as the specification continues.

Figure 1:
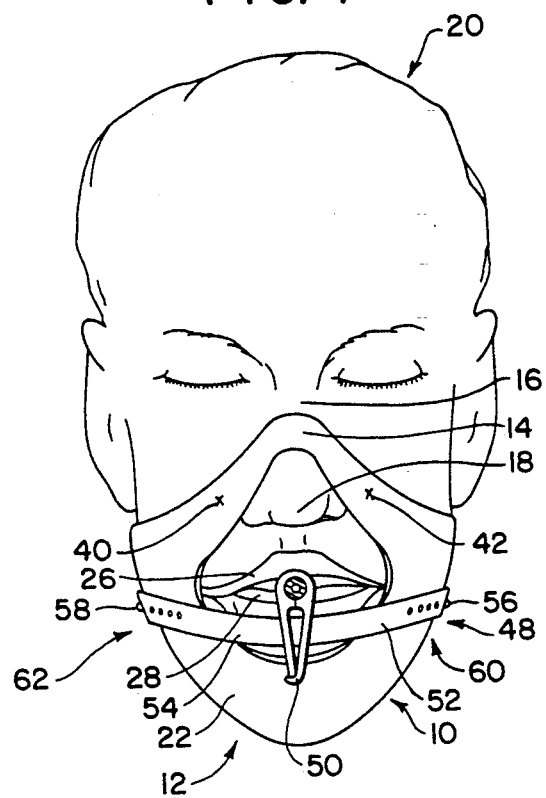
FIG. 1 is a front elevational view showing the mechanism of the present invention in place on a patients head.

For a better understanding of the invention, reference is made to the following Detailed Description of the Preferred Embodiments thereof which should be taken in conjunction with the hereinabove described drawings.

DETAILED DESCRIPTION OF THE PREFERRED EMBODIMENTS

Various aspects of the present invention will evolve from the following Detailed Description of the Preferred Embodiments which should be referenced to the prior described drawings.

The invention as a whole is depicted in the drawings by reference character 10. The tracheal tube support mechanism 10 includes as one of its elements, a facial cover 12 which is constructed of relatively pliable material, such a silicone, rubber, polyethylene, cloth, and the like. The facial cover 12 possesses a first portion 14 which extends over the bridge 16 of the nose 18 of the user's head 20, FIG. 1 ,A connected second portion 22 extends over the chin of the user's head 20 and is connected to the first portion 14. An opening 24 of facial cover 12 permits tactile access to nose 18 and lips 26 of mouth 28.

Figure 2:
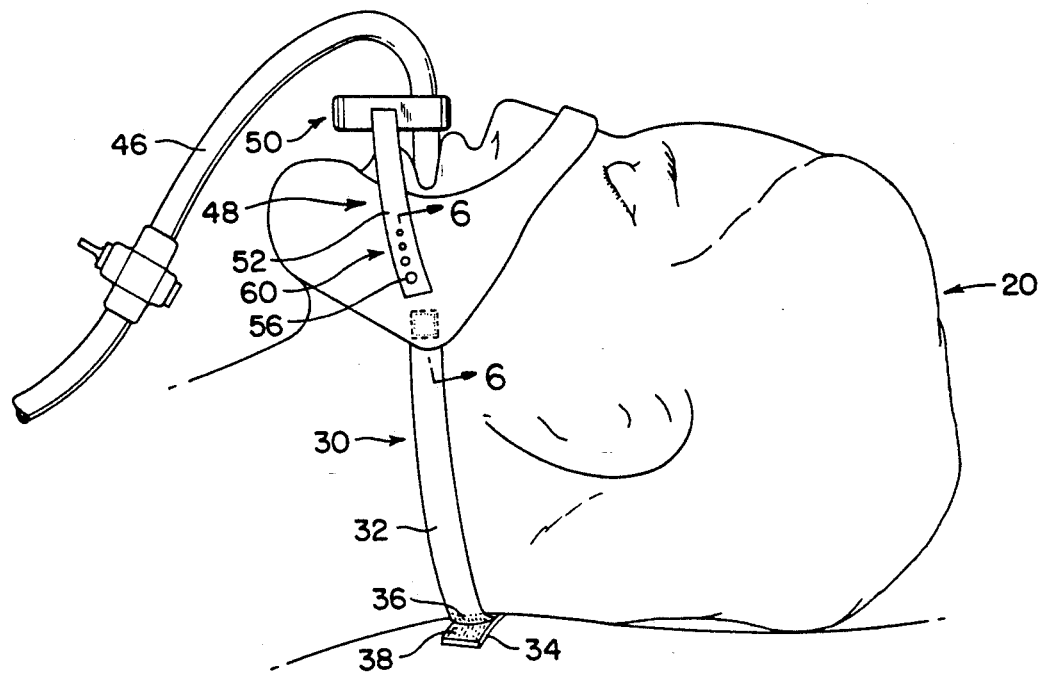
FIG. 2 is a right-side elevational view of the mechanism of the present invention in place on a patient's head.

Means 30 for holding facial cover 12 to head 20 is also depicted in the drawings, FIG. 2. Means 30 may take the form of straps 32 and 34 which are attached to facial cover 12 and adjustably connected with VELCRO strips 36 and 38 at the ends thereof. Of course, other fastening means may be employed in substitution for VELCRO strips 36 and 38 such as snaps, buttons, lines capable of being tied, and the like. In essence, means 30 holds facial cover 12 to head 20 without applying substantial pressure to bridge 16 of nose 18. Pressure points 40 and 42, FIG. 1 represent the places of intended application of pressure on head 20 by facial cover 12.

Figure 6:
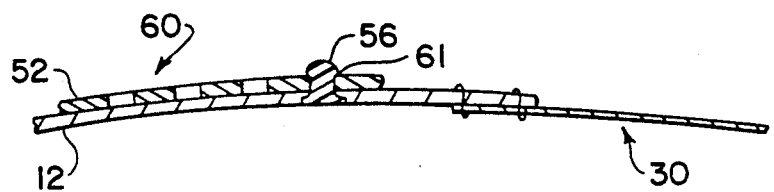
FIG. 6 is a sectional view taken along lines 6-6 of FIG. 2.

Means 44 is also revealed in the present invention for positioning tracheal tube 46 within the mouth 28 of head 20. Of course, tracheal tube 46 extends into the trachea and is maintained in an open position by a known inflation mechanism (not shown). For example, an endo-tracheal tube manufactured by Mallinckrodt, Inc. of Glenn Falls, N.Y., may suffice in this regard. Means 44 may externalize in an element 48 which is linked to the facial cover 12 and is connected to the tracheal tube 46 by a fastener 50. Element 48 may include a single leg 52 of a relatively stiff configuration, or an additional leg 54. In the latter case, legs 52 and 54 would extend from the facial cover 12 to fastener 50 on either side of nose 18 of head 20. Protuberances 56 and 58 extending from facial mask 12 would engage a plurality of openings 60 and 62 on legs 52 and 54 of element 48, respectively. For example, protuberance 56 is depicted as engaging an opening 61 through element 52 in FIG. 6. Thus, the fastener 50 and the attached tracheal tube 46 are held against movement of tracheal tube from mouth 28.

Figure 3:
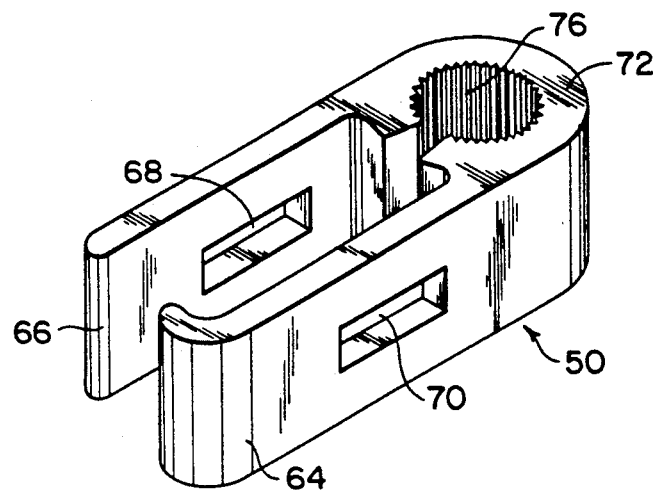
FIG. 3 is a perspective view of the tracheal tube fastener employed in the mechanism of the present invention.
Figure 4:
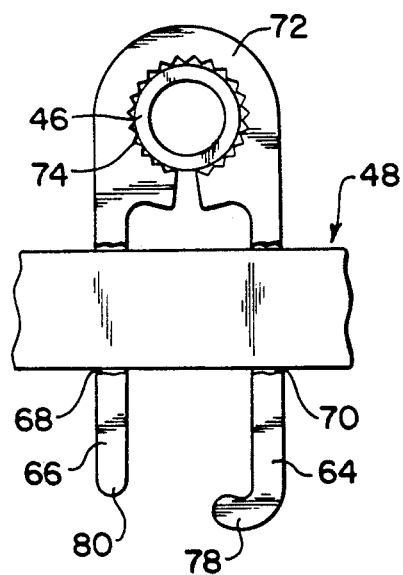
FIG. 4 is a front elevational view of the fastener of FIG. 3 employed with a tracheal tube prior to the exertion of a clamping pressure.
Figure 5:
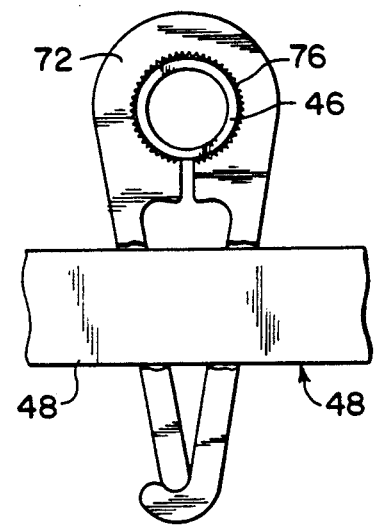
FIG. 5 is a front elevational view of the fastener of FIG. 3 clamped to a tracheal tube and spanning element.

Turning to FIGS. 3-5, fastener 50 is described in detail. Fastener 50 is formed with a pair of flanges 64 and 66 having aligned slots 68 and 70, therethrough. Flanges 64 and 66 are resiliently attached to bend 72. Bend 72 forms an aperture 74 possessing an inner striated surface 76. As shown in FIGS. 4 and 5, element 48 extends through slots 68 and 70 while tracheal tube 46 is encompassed by aperture 74 Hook 78 of flange 64 engages end 80 of flange 66 to retain tightened striated surface 76 about tracheal tube 46, FIG. 5. In addition, slots 68 and 70 hold element 48 against slippage through the same.

In operation, first portion 14 of facial cover 12 is placed over bridge 16 of nose 18 of head 20. Simultaneously, second portion 22 of facial cover 12 is placed over the chin of head 20 as depicted in FIGS. 1 and 2. Straps 32 and 34 connected to facial cover 12 are extended about the back of head 20 and attached VELCRO strips 36 and 38 to a predetermined tension. Fastener 50 is clamped to tracheal tube 46 which is placed in the trachea of the patient. Legs 52 and 54 of element 48 are then adjustably fastened to protuberances 56 and 58 extending from facial mask 12 by the use of plurality of openings 60 and 62. Thus, tracheal tube 46 is positioned within the mouth 28 of head 20 and prevented from moving laterally relative to nose 18, FIG. 1, by fastener 50. Likewise, tracheal tube 46 is prevented from moving from the trachea by fastener 50 and, in particular, the holding action of striated surface 76 of fastener 50.

While, in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A tracheal tube support and retention device for holding a tracheal tube within the mouth of a user, which device comprises:
 a) a facial cover including a first portion extending over the nasal bridge of a user, a second portion extending over the chin of a user, said first portion being connected to said second portion, said facial cover also having an opening therein between said first and second portions to permit access to the nostrils of the nose and to the mouth of said user;
 b) retaining means for positioning the tracheal tube within the mouth of a user to resist the removal of the tracheal tube therefrom; said means comprising a fastener held in position in front of the mouth of the user, said fastener having a pair of spaced resilient flanges each of which flanges has an aligned slot therethrough, one of which flanges is releaseably engageable with the other,
 said fastener having a constrictable opening in communication with the space between said flanges, for receipt of said tracheal tube,
 whereby when said flanges are engaged, the constrictable opening is constricted to thereby retain the tracheal tube, and when said flanges are disengaged, the tracheal tube is axially moveable within said constrictable opening;
 c) holding means for holding said facial cover to the head of a user, said holding means being secured to said facial cover and passing through said aligned slots of the fastener, such that said holding means is held normal to said fastener.

2. The tracheal tube support and retention device of claim 1 wherein the constrictable opening in said fastener is serrated for improved gripping.

3. The tracheal tube support and retention device of claim 1 further comprising means for adjusting said holding means to securely hold the facial cover to the head of a user.

4. The tracheal tube support and retention device of claim 1 wherein said facial cover is constructed of relatively pliable material and said fastener is constructed of relatively rigid material.

* * * * *